United States Patent [19]
Van Broekhoven et al.

[11] Patent Number: 5,986,158
[45] Date of Patent: Nov. 16, 1999

[54] PROCESS FOR ALKYLATING HYDROCARBONS

[75] Inventors: Emanuel Hermanus Van Broekhoven, Monnickendam; Francisco Rene Mas Cabre, Amstelveen; Pieter Bogaard, Broek in Waterland; Gijsbertus Klaver, Ilpendam; Marco Vonhof, Purmerend, all of Netherlands

[73] Assignee: Akzo Nobel NV, Anrhem, Netherlands

[21] Appl. No.: 08/974,762

[22] Filed: Nov. 20, 1997

Related U.S. Application Data

[60] Provisional application No. 60/031,542, Dec. 2, 1996.

[30] Foreign Application Priority Data

Nov. 27, 1996 [NL] Netherlands ............................ 1004623
Sep. 25, 1997 [EP] European Pat. Off. .............. 97202951

[51] Int. Cl.[6] ................................ C07C 2/58; C07C 2/56; B01J 20/34
[52] U.S. Cl. .......................... 585/722; 585/709; 585/721; 585/730; 585/731; 502/30; 502/31; 502/53; 502/56
[58] Field of Search .................................... 585/709, 722, 585/401, 730, 731, 721; 502/30, 31, 53, 56

[56] References Cited

U.S. PATENT DOCUMENTS

| | | | |
|---|---|---|---|
| 3,549,557 | 12/1970 | Bolton et al. ........................... | 252/455 |
| 3,851,004 | 11/1974 | Yang ..................................... | 260/671 C |
| 5,489,732 | 2/1996 | Zhang et al. .............................. | 502/31 |

FOREIGN PATENT DOCUMENTS 0 688 749  12/1995  European Pat. Off. .......... C07C 2/58

OTHER PUBLICATIONS

Abstract, EP 688749–A1, dated Dec. 27, 1995.
*International Search Report,* dated Jun. 23, 1997.

*Primary Examiner*—Walter D. Griffin
*Assistant Examiner*—In Suk Bullock
*Attorney, Agent, or Firm*—Oliff & Berridge, PLC

[57] ABSTRACT

The invention pertains to a process for alkylating hydrocarbons in which an alkylatable organic compound is reacted with an alkylation agent to form an alkylate in the presence of a catalyst comprising a hydrogenating function and a solid acid constituent, with the catalyst being subjected intermittently to a regeneration step by being contacted with a feed containing a saturated hydrocarbon and hydrogen, said regeneration being carried out at 90% or less of the active cycle of the catalyst, with the active cycle of the catalyst being defined as the time from the start of the feeding of the alkylation agent to the moment when 20% of the alkylation agent leaves the catalyst-containing reactor section without being converted, not counting isomerization inside the molecule. The process according to the invention is especially attractive for the alkylation of isobutane with one or more butenes to form an alkylate with a high RON.

24 Claims, 1 Drawing Sheet

Figure 1: 1.5 mm diameter extrudate
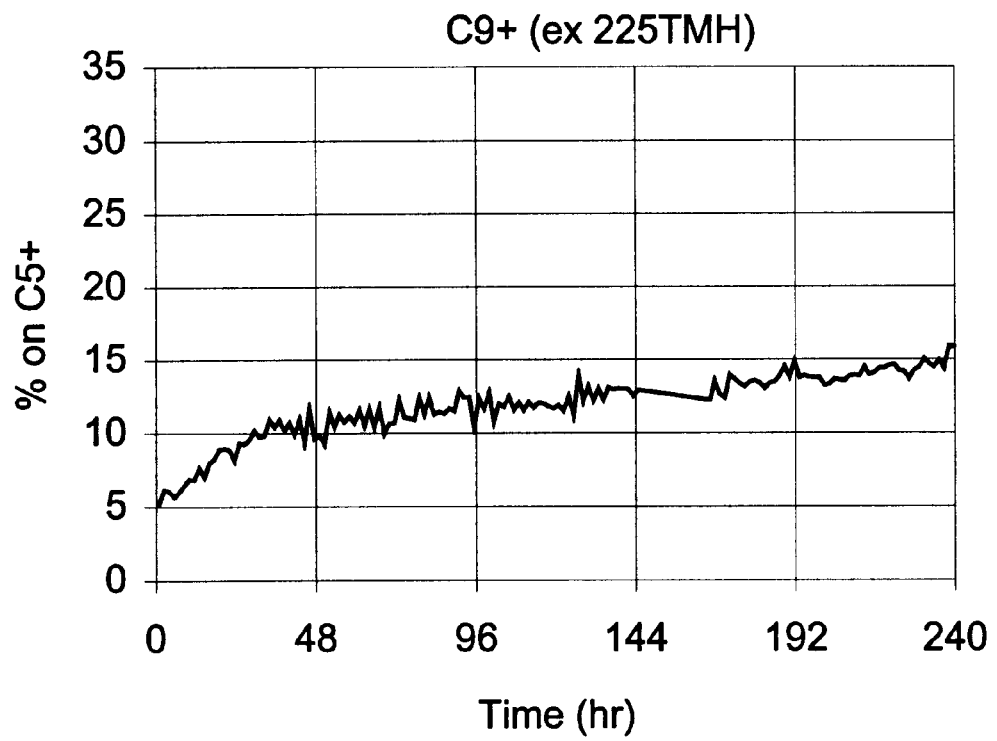
Figure 2: 3 mm diameter extrudate
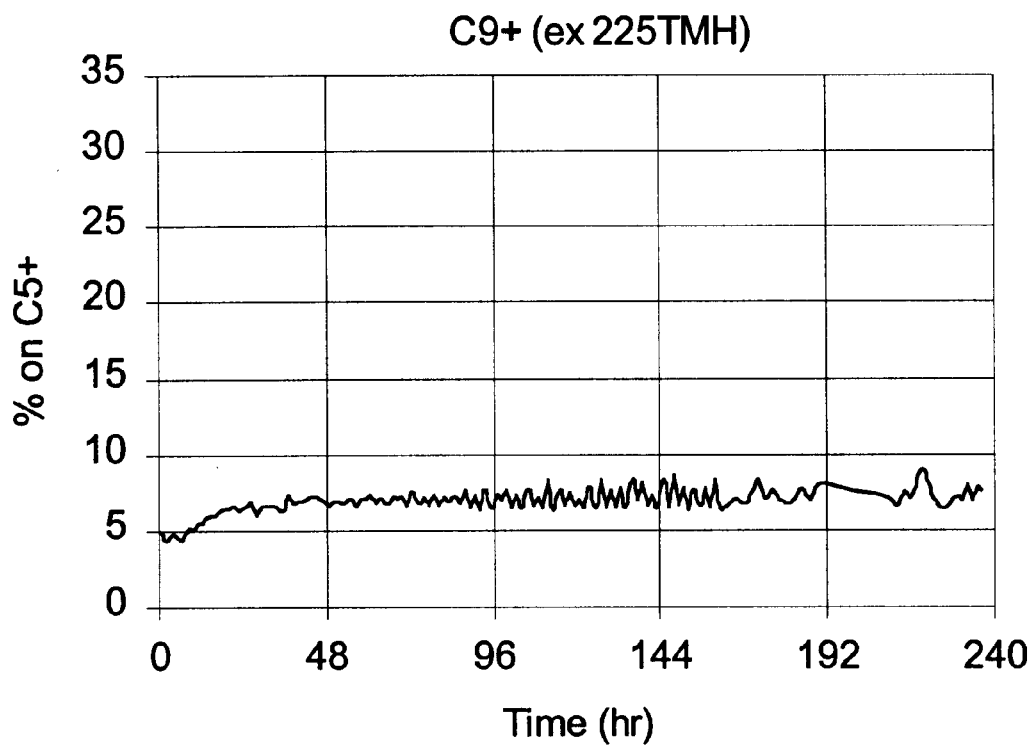

PROCESS FOR ALKYLATING HYDROCARBONS

The present invention claims priority of Dutch application No. 1004623 filed Nov. 27, 1996 and European application No. 97202951 filed Sep. 25, 1997, and benefit of U.S. Provisional application No. 60/031,542 filed Dec. 2, 1996.

The present invention relates to a process for alkylating hydrocarbons, more particularly to a process for alkylating aliphatic hydrocarbons, in the presence of a catalyst comprising a hydrogenating function and a solid acid constituent.

The term alkylation within the framework of the present invention refers to the reaction of a saturated hydrocarbon, in general a branched saturated hydrocarbon, with an olefin to give highly branched saturated hydrocarbons with a higher molecular weight. In particular, this reaction is of interest because it makes it possible to obtain, through the alkylation of isobutane with an olefin containing 2–6 carbon atoms, an alkylate which has a high octane number and which boils in the gasoline range. Unlike gasoline obtained by cracking heavier petroleum fractions such as vacuum gas oil and atmospheric residue, gasoline obtained by alkylation is essentially free of contaminants such as sulphur and nitrogen and so has clean burning characteristics. Its high anti-knock properties, represented by the high octane number, lessen the need to add environmentally harmful anti-knock compounds such as lead. Also, unlike gasoline obtained by reforming naphtha or by cracking heavier petroleum fractions, alkylate contains few if any aromates or olefins, which, environmentally speaking, is a further advantage.

The alkylation reaction is acid-catalysed. At present, in commercial alkylation equipment use is made of liquid acid catalysts such as sulphuric acid and hydrogen fluoride. The use of such catalysts is attended with a wide range of problems. For instance, sulphuric acid and hydrogen fluoride are highly corrosive, so that the equipment used has to meet high quality requirements. Since the presence of highly corrosive materials in the resulting fuel is objectionable, the remaining acid has to be removed from the alkylate. Also, because of the phase separations which have to be carried out, the process is complicated and thus expensive. Besides, there is always the risk that toxic substances such as hydrogen fluoride will be emitted.

To prevent these problems, the use of solid acid catalysts such as zeolite-containing catalysts in alkylation reactions has long been the subject of research. A significant problem when using these catalysts in alkylation is their very rapid deactivation, which is attributed to the formation of polyalkylates which are converted into coke. A number of methods for regenerating solid acid catalysts have been developed, but none of these methods is at the same time both effective and simple enough to permit the use of solid acid catalysts on a commercial scale. Thus it is known to regenerate a deactivated zeolite-containing catalyst at high temperature, e.g., from 200 to 400° C., with hydrogen in the gas phase. This regeneration method is capable of restoring the catalyst's activity to its original level. However, when this regeneration method is employed, the reactants and the product have to be removed from the reactor, the reactor has to be heated up to temperature, hydrogen gas has to be passed through it at high temperature, the reactor has to be cooled down again after regeneration, the supply of hydrogen has to be stopped, and the reactor has to be refilled with the reactants. A commercial process in which the catalyst has to be regenerated in this manner every time it deactivates is not attractive for use on a commercial scale.

Alternatively, U.S. Pat. No. 3,549,557 describes a process for alkylating isobutane with an olefin in which the zeolite-containing catalyst is regenerated by being washed with isobutane in the absence of olefin, optionally with heating. In the event of the catalyst becoming seriously coked, it is regenerated by heating in the presence of oxygen. It is put forward in this publication that polyalkylate formation can be prevented by recurrent washing of the catalyst with isobutane. This is said to give a longer catalyst cycle. However, the experiments described in this publication show that by this method the total reaction time prior to catalyst deactivation can be increased from 10 to 14 hours only. This regeneration method is thus not satisfactory for commercial operation.

U.S. Pat. No. 3,815,004 describes a process for alkylating hydrocarbons in which an olefin is reacted with an alkylatable organic compound in the presence of a catalyst containing a Group VIII hydrogenation metal and a zeolite. When the activity of the catalyst has decreased to an unacceptable level, it is regenerated by being contacted with a solution of hydrogen in alkane in the absence of olefin. Experiments have shown that regenerating the catalyst in this fashion when the activity of the catalyst has decreased to an unacceptable level, that is after olefin has been found in the product leaving the reactor, a process is obtained which can be used for a few cycles only before unacceptable results are obtained. Moreover, the reaction yield was found to be low. In the examples yields of 133–136 wt. % are obtained, calculated on olefin.

The present invention provides a process for alkylating hydrocarbons which makes it possible to produce an alkylate of good quality in a commercially interesting manner over a long period of time in high yield.

In the process according to the invention an alkylatable organic compound is reacted with an alkylation agent to form an alkylate in the presence of a catalyst comprising a hydrogenating function and a solid acid constituent, with the catalyst being subjected intermittently to a regeneration step by being contacted with a feed containing a saturated hydrocarbon and hydrogen, said regeneration being carried out at 90% or less of the active cycle of the catalyst. The active cycle of the catalyst is defined as the time from the start of the feeding of the alkylation agent to the moment when 20% of the alkylation agent, relative to the concentration at the entrance of the catalyst-containing reactor section, leaves the catalyst-containing reactor section without being converted, not counting isomerisation within the molecule.

The crux of the process according to the invention resides in the fact that the catalyst is regenerated before there is any substantial decrease of its activity. It was found that this results in a process capable of producing a high yield of high-quality alkylate over a very long period of time, while the regeneration is easy to carry out.

Because the catalyst is regenerated with a feed containing a saturated hydrocarbon and hydrogen, the process can be run virtually continuously without the need to change over from the liquid phase to the gas phase and vice versa, this in contradistinction to a regeneration with hydrogen gas at elevated temperature. Because there is no need to heat and cool the reactor, the process requires less energy. In addition, as the catalyst does not contain any volatile or loosely bound constituents, as in the case of liquid acids on a solid carrier, the process according to the invention is attended with fewer environmental hazards than other processes.

Furthermore, the process according to the invention is a flexible one. If, owing to circumstances, the catalyst deactivates to an unacceptable extent during the process, it can be regenerated in the conventional manner by contacting it at high temperature with hydrogen in the gas phase to recover its original activity. The catalyst can then be used again in a process according to the invention with intermittent regeneration employing a feed which contains a saturated hydrocarbon and hydrogen. The high temperature regeneration is effected at a temperature of at least 175° C., preferably in the range of 175–600° C., more preferably 200–400° C. To effect a long term process on commercial scale one can, e.g., carry out such a high temperature regeneration after every 50 regenerations with saturated hydrocarbon and hydrogen, preferably after every 100. Pilot plant experiments have shown that it is possible to effect a long term process when the catalyst is subjected to a high temperature regeneration after every 200–400 regenerations with saturated hydrocarbon and hydrogen. Depending on the exact process variables on commercial scale this value may in practice be higher or lower.

The process according to the invention gives a product of nearly constant composition with a high yield. In processes according to the prior art, where the catalyst was not regenerated until after olefin breakthrough, that is after olefin is found in the product leaving the reactor, the yield of C5+ alkylate decreases markedly after breakthrough, while the amount of undesired C9+ by-product increases. By regenerating prior to olefin breakthrough it is possible to maintain a high C5+ alkylate yield with a high octane number, while the amount of C9+ can be restricted. In consequence, when the process according to the invention is employed, little product of low quality and hence reduced economic value will be produced.

The catalyst used in the process according to the invention comprises a hydrogenation function and a solid acid constituent. Examples of suitable hydrogenating functions are constituents of the transition metals, such as metals of Group VIII of the Periodic Table, or mixtures thereof.

Among these, noble metals of Group VIII of the Periodic Table are preferred. Platinum, palladium, and mixtures thereof are especially preferred. The amount of hydrogenating function will be dependent on its nature. When the hydrogenating function is a noble metal of Group VIII of the Periodic Table, the catalyst generally will contain in the range of 0.01 to 2 wt. % of the metal, preferably 0.1–1 wt. %, calculated as metal.

Examples of solid acid constituents are zeolites such as Y-zeolites, including H-Y-zeolites and USY-zeolites, zeolite beta, MCM-22, and MCM-36, non-zeolitic solid acids such as silica-alumina, sulphated oxides such as sulphated oxides of zirconium, titanium, or tin, sulphated mixed oxides of zirconium, molybdenum, tungsten, etc., and chlorinated aluminium oxides. The presently preferred solid acid constituents are zeolites, including Y-zeolites and zeolite beta, sulphated oxides, and chlorinated aluminium oxides. Mixtures of solid acid constituents can also be employed.

Surprisingly it has been found that it is preferred for the catalyst to be used in the process according to the invention to comprise a matrix material. In the art of catalysis, it is generally expected that the incorporation of matrix into a catalyst particle will decrease the activity of the catalyst in comparison with a catalyst particle which contains only the active component, e.g., a solid acid constituent. This is because the matrix "dilutes" the active component. One expects that the selectivity of the catalyst will remain substantially the same when a relatively inert matrix material, such as alumina, is incorporated into the catalyst particle. However, for the present case it has surprisingly appeared that the incorporation of a matrix component into the catalyst composition leads to an increase in Research Octane Number (RON). The increase in RON reflects an increase in the selectivity for compounds with a high RON.

Accordingly, the catalyst to be used in the process according to the invention preferably comprises a hydrogenating function on a carrier which comprises 2–98wt. % of solid acid constituent and 98–2 wt. % of a matrix material, calculated on the carrier. Preferably, the carrier comprises 10–90 wt. % of matrix material, and 90–10 wt. % of solid acid constituent. More preferably, the carrier comprises 20–80 wt. % of matrix material and the balance solid acid constituent. Especially preferred is the catalyst wherein in the carrier comprises 20–50 wt. % of matrix material and the balance solid acid constituent.

In the present specification the term matrix material encompasses all components which are present in the catalyst except for the solid acid constituent and the hydrogenation metal component. Examples of suitable matrix materials are alumina, silica, clays, and mixtures thereof. Matrix materials comprising alumina are generally preferred. A matrix material which consists essentially of alumina is considered most preferred at this point in time.

It has also been found, and again surprisingly, that an increase in the particle size of the catalyst particle leads to an increase in selectivity and stability of the catalyst to be used in the process according to the invention. When dealing with diffusion-limited reactions, including the alkylation reaction with a highly acidic catalyst in the liquid phase, the person skilled in the art of catalysis will generally expect that the effective volume activity of a catalyst will decrease when the particle size of the catalyst increases. The reasoning behind this is as follows. When the size of a catalyst particle increases, it will take longer for the reactants to reach all active sites of the catalyst particle. This will decrease the activity of the catalyst. Further, it is expected that when the size of a catalyst particle increases, it will take longer for the product of the reaction to leave the catalyst particle, leading to an increased risk of side reactions, and therefore a decrease in selectivity. Because the secondary products formed by these side reactions will also take longer to leave the catalyst, the risk that these products will be converted into coke also increases. Coke formation decreases the stability of the catalyst.

In the art of alkylation, these considerations have caused people working in this field to develop slurry-type processes in which relatively small catalyst particles are applied.

However, for the present process it has surprisingly been found that if the particle size of the catalyst particles is increased from e.g., a value of about 0.5 mm to a value above 0.75 mm, the quality of the C8-alkylate produced is improved, as is evidenced by an increased RON. Further, it appears that the amount of C9+ alkylate formed with time decreases. Since C9+ alkylate is produced along reaction pathways which may also lead to coke, a decrease in the formation of C9+ alkylate is an indication for an increase in the stability of the catalyst.

Accordingly, the catalyst to be used in the process according to the invention preferably has a particle size of at least 0.75 mm. Preferably, the particle size is at least 1.5 mm, more preferably at least 2.5 mm. The upper limit of the particle size preferably lies at 15 mm, more preferably at 10 mm, even more preferably at 8 mm. In the present specification, the term particle size is defined as the average diameter of the solid part of the catalyst, as will be clear to the skilled person.

The catalyst can be prepared by processes common to the industry. These will comprise, say, shaping the solid acid constituent after mixing it with a matrix material, to form particles, followed by calcination of the particles. The hydrogenating function may, e.g., be incorporated into the catalyst composition by impregnating the carrier particles with a solution of a hydrogenation metal component.

The active cycle value and the alkylate yield in a particular process will depend on the nature and the properties of the catalyst, but also on the process conditions. As indicated above, the active cycle for a given catalyst and given process conditions is defined as the time from the start of the feeding of the alkylation agent to the moment when, in comparison with the entrance of the catalyst-containing reactor section, 20% of the alkylation agent leaves the catalyst-containing reactor section without being converted, not counting isomerisation within the molecule. The C5+ alkylate yield is defined as the weight amount of C5+ alkylate produced divided by the overall weight of olefin consumed. This number is often expressed as a percentage.

The process according to the invention is particularly suited to be used for alkylating isoalkanes having 4–10 carbon atoms, such as isobutane, isopentane or isohexane or mixtures thereof, with olefins having 2–10 carbon atoms, preferably 2–6 carbon atoms, more preferably 3–5 carbon atoms. The alkylation of isobutane with butene or a mixture of butenes constitutes an attractive embodiment of the process according to the invention.

As will be evident to the skilled person, the process according to the invention can be applied in any suitable form, including fluidised bed processes, slurry processes and fixed bed processes, with fixed bed processes being preferred. The process may be carried out in a number of beds, each with separate olefin addition. In such a case, the process of the invention may be carried out in each separate bed.

The alkylation process is practiced under conditions such that at least a portion of the alkylation agent and the alkylatable compound will be in the liquid phase or the supercritical phase. In general, the process according to the invention is practiced at a temperature in the range of −40 to 250° C., preferably in the range of 50 to 150° C., more preferably in the range of 75 to 95° C., and a pressure of from 1 to 100 bar, preferably of from 10 to 40 bar, more preferably of from 15 to 30 bar. The molar ratio of alkylatable compound to alkylation agent in the total feed in the reactor preferably is higher than 5:1, more preferably higher than 50:1. Higher molar ratios are considered preferred for performance reasons, because they generally yield an increase in octane number and stability. The upper limit for this ratio is determined by the type of process applied, and by the process economics. It is not critical, and may be as high as 5000:1. Generally, figures of, e.g., 1000:1 or lower are preferred. At this moment a molar ratio of alkylatable compound to alkylation agent of 150–750:1 is considered most preferred. The feed rate (WHSV) of the alkylation agent generally is in the range of 0.01 to 5, preferably in the range of 0.05 to 0.5, more preferably in the range of 0.1 to 0.3 grams of alkylation agent per gram of catalyst per hour. The WHSV of the alkylatable saturated hydrocarbon preferably is in the range of 0.1 to 500 $h^{-1}$.

As will be evident, the essential components to be present in the reaction medium during the alkylation reaction are the alkylatable organic compound and the alkylation agent. Of course, the reaction medium will also contain the reaction products formed. The reaction may be carried out in the substantial absence of other components in the reaction medium. However, the reaction medium may contain other components, generally in minor amounts, as long as they do not detrimentally affect the alkylation reaction. In particular, the reaction medium may contain a small amount of hydrogen, e.g., as relict from the regeneration step. A too high amount of hydrogen should be avoided, because it will interfere with the alkylation reaction by reacting with the alkylation agent. Nevertheless, trace amounts of hydrogen can be accepted, and may sometimes be beneficial.

The catalyst is regenerated by being contacted with a mixture of hydrogen and a saturated hydrocarbon. The mixture of hydrogen and saturated hydrocarbon generally takes the form of a solution of hydrogen in the hydrocarbon. Preferably, the solution contains at least 10% of the saturation concentration of hydrogen, said saturation concentration being defined as the maximum quantity of hydrogen which can be dissolved in the saturated hydrocarbon at regeneration temperature and pressure. More preferably, the solution will contain at least 50% of the saturation concentration, more preferably still at least 85%. Because of the hydrogen's regenerative action, it is generally preferred to have as saturated a solution of hydrogen in saturated hydrocarbon as possible, since this will reduce the regeneration time.

As to the nature of the saturated hydrocarbon used in the regeneration process, the following is noted. In principle, use may be made of any linear, branched or cyclic saturated hydrocarbon, or mixtures thereof which are liquid or in the supercritical condition at regeneration temperature and pressure. In actual practice, it is preferred as a rule to employ the alkylatable compound as saturated hydrocarbon in the regeneration, since in that case there is no need to add an extra constituent to the system. A further advantage in that case is that the effluent from the regeneration step can be added to the regular alkylate stream.

In general, the regeneration step is carried out at a temperature in the range of −40 to 250° C., a pressure of from 1 to 100 bar, and a WHSV of the saturated hydrocarbon in the range of 0.1 to 500 $h^{-1}$. When the saturated hydrocarbon used in the regeneration is the alkylatable compound, it is preferred to have the regeneration conditions differ as little as possible from the reaction conditions. This facilitates the performance of the reaction. In that case it is preferred for the regeneration temperature to differ from the reaction temperature, expressed in ° C., by not more than 50%, more preferably by not more than 20%, still more preferably by not more than 10%, for the regeneration pressure to differ from the reaction pressure by not more than 50%, more preferably by not more than 20%, still more preferably by not more than 10%, and, in particular for fixed bed processes, for the regeneration-WHSV to differ from the reaction-WHSV by not more than 50%, more preferably by not more than 20%, still more preferably by not more than 10%. Even more preferably, the temperature, the pressure, and, in particular for fixed bed processes, the WHSV of the saturated hydrocarbon during the regeneration are essentially the same as the temperature, the pressure, and the WHSV of the saturated hydrocarbon during the reaction. This facilitates the performance of the process as a whole in an economic manner. In some cases, however, it may be attractive to carry out the regeneration at a higher temperature or pressure than the reaction step. Alternatively, the regeneration may be carried out under supercritical conditions. However, carrying out the regeneration step and the reaction step under different conditions will always entail a less readily controllable change from one step to the other.

The duration of the regeneration step is dependent on a number of conditions, including the nature of the catalyst, the duration of the reaction step, the reaction conditions, the regeneration conditions, and the amount of hydrogen which is present during the regeneration step. In general, it holds good that the shorter the reaction step is, the shorter the regeneration step may be. A higher regeneration frequency will also result in a more effective regeneration. Furthermore, the regeneration step may be shortened as the regeneration solution of hydrogen in saturated hydrocarbon contains more hydrogen. Generally speaking, the length of the regeneration step is in the range of 0.1 to 10 times the length of the reaction step, preferably in the range of 0.5 to 2 times the length of the reaction step. The amount of $H_2$ consumed per regeneration step is dependent, int. al., on the duration of the regeneration step and the $H_2$ concentration in the saturated hydrocarbon. In general, it is 0.001–0.25 moles of $H_2$ per gram of catalyst per regeneration.

Preference is given to the introduction of a washing step between the reaction step and the regeneration step, between the regeneration step and the reaction step, or on both occasions, in which washing step the catalyst is washed with a saturated hydrocarbon essentially free of alkylation agent and hydrogen. As with the regeneration step it is possible, in principle, to employ any linear, branched or cyclic saturated hydrocarbon or mixtures thereof which are liquid or in supercritical condition under washing conditions. In actual practice, also in the case of the washing step it is generally preferred to employ the alkylatable compound as saturated hydrocarbon, since this avoids adding an extra constituent to the system. The washing step is performed to facilitate the change from the reaction step, in which a mixture of an alkylatable compound and an alkylation agent is supplied, to the regeneration step, in which a mixture of a saturated hydrocarbon, preferably the alkylatable compound, and hydrogen is supplied. The introduction of a washing step prevents the olefinic alkylation agent from coming into contact with the hydrogen, a contact which would generally lead to a reaction between the olefin and the hydrogen to form alkane.

As a rule, the washing step is carried out at a temperature in the range of −40 to 250° C., a pressure of from to 1 to 100 bar, and a WHSV of the saturated hydrocarbon in the range of 0.1 to 500 $h^{-1}$. When the saturated hydrocarbon used during the washing step is the alkylatable compound, it is preferred to have the least possible difference between the washing conditions and the reaction conditions. This facilitates the performance of the process.

In that case it is preferred for the washing temperature to differ from the reaction temperature, expressed in ° C., by not more than 50%, more preferably by not more than 20%, still more preferably by not more than 10%, for the washing pressure to differ from the reaction pressure by not more than 50%, more preferably by not more than 20%, still more preferably by not more than 10%, and, in particular for fixed bed processes, for the washing-WHSV to differ from the reaction-WHSV by not more than 50%, more preferably by not more than 20%, still more preferably by not more than 10%. More preferably, the temperature, the pressure, and, in particular for fixed bed processes, the WHSV of the saturated hydrocarbon during the washing step, as during the regeneration step, are essentially the same as the temperature, the pressure, and the WHSV of the saturated hydrocarbon during the reaction.

When the reaction conditions differ from the regeneration conditions, it is attractive to select conditions for the washing step which are intermediate between the conditions at which the reaction is carried out and the conditions at which the regeneration is carried out. Alternatively, it is possible to have the conditions, such as temperature and pressure, of the washing step gradually change over from the conditions of the reaction step to the conditions which prevail during the regeneration step, or vice versa. All this enables proper process control.

The duration of the washing step is chosen such that olefin and hydrogen remain essentially separated from each other. As a rule, the duration of the washing step is at the most as long as the duration of the regeneration step. The duration of the washing step preferably is 0.01 to 1 times as long as the duration of the regeneration step.

Some words on the startup of the process are considered appropriate. It has been found that it may be advantageous to start up the process at a temperature which is lower than the temperature at which the process will be carried out. The advantage of this procedure is that the catalyst is slightly deactivated by being used at low temperatures during startup. This may result in less undesired side reactions.

The regeneration is performed on 90% or less of the active cycle of the catalyst, preferably on 60% or less, more preferably on 35% or less, more preferably still on 20% or less, most preferably on 10% or less. In general, preference is given to frequent catalyst regeneration, since this benefits the quality of the product formed and makes it possible to reduce the regeneration time. As the regeneration procedure is easily included in the process, regeneration on a regular basis is feasible. The optimum regeneration frequency in a specific case will depend on the nature of the catalyst and the process conditions and can easily be determined by the skilled person.

As the catalyst is regenerated more frequently, the resulting product will contain less C9+ alkylate. C9+ alkylate is produced along reaction pathways which may also lead to coke formation. A higher amount of C9+ alkylate may thus be accompanied by catalyst deactivation. The C5+alkylate obtained using the process according to the invention preferably has a C9+ content of less than 30 wt. %, more preferably of less than 20 wt. %, most preferably of less than 10 wt. %. Frequent catalyst regeneration enables C9+ production to be controlled at a comparatively low level.

Also, depending on the regeneration frequency, in the process according to the invention a high C5+ alkylate yield is obtained. The process according to the invention makes it possible to obtain a C5+ alkylate yield in excess of 200%, calculated on the weight of the consumed olefin, preferably of 204% or higher.

The quality of the alkylate product obtained in the process according to the invention can be measured by the RON of the product. The RON is a measure of the anti-knock rating of gasoline and/or gasoline constituents. The higher the RON, the more favourable the anti-knock rating of the gasoline will be. Depending on the type of gasoline engine, generally speaking a higher anti-knock rating is of advantage when it comes to the working of the engine. The product obtained in the process according to the invention preferably has a RON of 90 or higher, more preferably of 92 or higher, most preferably 94 or higher. The RON is obtained by determining, e.g., via gas chromatography, the percentage by volume of the various hydrocarbons in the product. The percentages by volume are then multiplied by the RON contribution and summed up. The RON contribution of the different constituents of a hydrocarbon feed are listed in the table below.

| Compound | RON |
|---|---|
| isopentane | 93 |
| n-pentane | 61.8 |
| 2,2-dimethyl butane | 91.8 |
| 2,3-dimethyl butane | 104.3 |
| 2-methyl pentane | 73.4 |
| 3-methyl pentane | 74.5 |
| n-hexane | 24.8 |
| 2,4-dimethyl pentane | 83.1 |
| trimethyl butane | 112.1 |
| 2-methyl hexane | 42.4 |
| 2,3-dimethyl pentane | 91.1 |
| 3-methyl hexane | 52 |
| 2,2,4-trimethyl pentane | 100 |
| n-heptane | 0 |
| 2,5-dimethyl hexane | 55.5 |
| 2,4-dimethyl hexane | 65.2 |
| 2,2,3-trimethyl pentane | 109.6 |
| 2,3,4-trimethyl pentane | 102.7 |
| 2,3,3-trimethyl pentane | 106.1 |
| 2,3-dimethyl hexane | 71.3 |
| 2-methyl heptane | 21.7 |
| 3,4-dimethyl hexane | 76.3 |
| 3-methyl heptane | 30 |
| 2,2,5-trimethyl hexane | 91 |
| total C9+ | 90 |

A related relevant parameter for product quality is the ratio of the amount of formed trimethyl pentanes (TMP) to the amount of formed dimethyl hexanes (DMH). Trimethyl pentanes have a RON of about 100–110. Dimethyl hexanes have a RON of about 60–70. Consequently, to obtain an alkylate with a high octane number, the highest possible TMP/DMH ratio is desired. The process according to the invention makes it possible to obtain a product having a TMP/DMH ratio of at least 2, preferably at least 3, more preferably at least 4.

COMPARATIVE EXAMPLE 1

This comparative example illustrates the effect of various regeneration methods applied after olefin breakthrough.

To evaluate the alkylation reactions use was made of a fixed-bed recycle reactor. This type of reactor is known to the skilled person. Its working principle is that a large portion of the effluent of the fixed-bed reactor is fed back to the reactor inlet. Here the effluent stream is combined with the reactant supply. In the following examples about 90% of the reactor effluent was fed back to the reactor. About 10% was separated from the main stream to determine the product properties.

A reactor having a diameter of 2 cm was filled with a 1:1 volume/volume mixture of 18 grams of catalyst (0.4–0.6 mm sieve fraction) and carborundum particles (60 mesh). The catalyst comprised a USY-zeolite as solid acid constituent and 0.5 wt. % of platinum as hydrogenating function. At the centre of the reactor tube a thermocouple of 6 mm in diameter was arranged. The reactor was flushed with nitrogen for 30 minutes (100 Nl/hour). Next, the system was tested for leakages at elevated pressure, after which the pressure was raised to 21 bar and the nitrogen replaced by hydrogen (100 Nl/hour). The reactor temperature was then raised to 200° C. at a rate of 1° C./min. After 1 hour at 200° C. the temperature was raised to 540° C. at a rate of 1° C./min. After 1 hour at 540° C. the reactor temperature was lowered to 90° C., which was the reaction temperature.

The hydrogen stream was stopped with the attaining of the reaction temperature. Isobutane was supplied to the reactor at a rate of about 880 gram/hour. 90% of the isobutane was fed back to the reactor. 10% was drained off for analysis. Such an amount of isobutane was supplied to the reactor to ensure a constant quantity of liquid in the system. When the system had stabilised, such an amount of cis-2-butene was added to it as to give a cis-2-butene-WHSV of 0.13 $h^{-1}$. The overall rate of flow of liquid in the system was maintained at about 880 g/h. The molar ratio of isobutane to cis-2-butene was about 364:1. The pressure in the reactor amounted to 21 bar.

The active cycle of the catalyst was determined by performing the process under the aforesaid conditions until at least 20% of the butene supplied was found in the product. Next, interpolation was used to determine the active cycle of the catalyst, i.e., it was established how much time passed between the start of the olefin supply and the moment when 20% of the alkylation agent, relative to the concentration at the entrance of the catalyst-containing reactor section, left the catalyst-containing reactor section without being converted, not counting isomerisation inside the molecule.

A number of experiments were carried out to investigate the regeneration method's effect on the active cycle of the catalyst. In all cases the catalyst was regenerated after 20% olefin breakthrough or more.

| | Regeneration conditions | | | |
|---|---|---|---|---|
| Exp. | medium | T (° C.) | P (bar) | t (h) | act. cycle (h) |
| 0 | fresh catalyst | | | | 10 |
| 1 | $H_2$ (71 Nl/h) gas phase | 250 | 21 | 1 | 10 |
| 1a | $H_2$ (71 Nl/h) gas phase | 250 | 21 | 1 | 10 |
| 1b | $H_2$ (71 Nl/h) gas phase | 250 | 21 | 1 | 10 |
| 2 | $H_2$ (1 mole %) in iso-butane | 90 | 21 | 66 | 6.5 |
| 3 | $H_2$ (1 mole %) in iso-butane | 115 | 30 | 18 | 4 |

Experiments 1, 1a, and 1b in the above table show that a catalyst which has been deactivated to the extent of there having been 20% or higher olefin breakthrough can be restored to its original activity by regeneration with hydrogen gas at a temperature of 250° C. This regeneration method enables multi-cycle use of the catalyst. However, each time this regeneration method is to be applied, the alkylate and C9+ have to be washed out of the system, the isoalkane has to be removed from the reactor, the reactor has to be heated up to temperature, hydrogen gas has to be passed through it at high temperature, the reactor has to be cooled down again after the regeneration, the supply of hydrogen has to be stopped, and the reactor has to be refilled with isoalkane. Such a regeneration method is unattractive for use on a commercial scale.

In experiments 2 and 3 a milder regeneration method was employed. The catalyst was contacted with a solution of hydrogen in isobutane for the specified period of time. Although the period of time selected was so long as to give rise to the expectation that proper catalyst regeneration had taken place, it was found that the length of the active cycle of the catalyst had decreased substantially when compared with the fresh catalyst and the catalyst regenerated with hydrogen at 250° C. Thus, these mild regeneration methods do not enable multi-cycle catalyst use.

EXAMPLE 1

This example illustrates the process according to the invention.

The process of Comparative example 1 was repeated using 27 grams of catalyst in a 1:1 volume ratio with 60 mesh carborundum particles, a total feed to the reactor of about 1320 gram/hour, a WHSV of the olefin of about 0.19 $h^{-1}$, and a ratio of olefin to isobutane of about 250:1. First, the active cycle of the catalyst was determined by running the system until 20% of the olefin left the catalyst bed unconverted. Under these conditions the active cycle turned out to be 7 hours.

Next, the catalyst was regenerated with hydrogen at a temperature of 250° C., as described above, returning the activity of the catalyst to its original level. The system was then started up again under the same conditions, except that each time after 1 hour of reaction, i.e., at 14% of the active cycle, the catalyst was regenerated by being washed with isobutane for 10 minutes, followed by 100 minutes of regeneration through being contacted with a solution of 1 mole % of $H_2$ in isobutane, and then being washed with isobutane for another 10 minutes (total washing and regeneration time 2 hours). The process conditions during the washing steps and the regeneration step were the same as the process conditions during the reaction step.

The quantity by weight of C5+ alkylate produced per gram of catalyst was used as a measure of the catalyst's and the regeneration method's quality. This number is also known in the field as catage. The catage is calculated as follows. Multiplying the C5+ alkylate yield, expressed as ratio, by the space velocity of the olefin gives the C5+ alkylate yield expressed in grams of C5+ alkylate per hour per gram of catalyst. Multiplying this C5+ alkylate yield by the number of hours of production gives the catage. Depending on the analytical method, it may be advisable to use the average C5+ alkylate yield, calculated by averaging the values obtained for the C5+ alkylate yield at various moments in the production cycle, to calculate the catage.

In this example after 40 cycles 17.4 grams of C5+ alkylate had been produced per gram of catalyst. At that time the system did not show any sign of olefin breakthrough, and the product quality and yield remained high.

The average product obtained in the course of this experiment had the following properties:

| | |
|---|---|
| C5+ alkylate yield | 229 wt. % |
| RON octane number | 91.2 |
| TMP/DMH | 2.9 |
| wt. % C9+ alkylate, calc. on C5+ alkylate (incl. 2,2,5-trimethyl hexane) | 11.4 |
| wt. % C8, calc. on C5+ alkylate | 58.2 |
| wt. % C5–C7, calc. on C5+ alkylate | 30.4 |
| Reid vapour pressure | 0.35 bar |
| density | 0.693 g/ml |

In comparable experiments run for a longer period of time a catage of more than 70 grams of C5+ alkylate per gram of catalyst was obtained.

COMPARATIVE EXAMPLE 2

This example illustrates that intermittent washing with isobutane does not lead to a stable process, in contradistinction to the process according to the invention, where intermittent regeneration with isobutane and $H_2$ is applied.

The process of Example 1 was repeated under the same condition, the only difference being that each time after 1 hour of reaction, i.e., at 14% of the active cycle, the catalyst was washed for two hours with isobutane, instead of being regenerated by being washed with isobutane for 10 minutes, followed by 100 minutes of regeneration through being contacted with a solution of 1 mole % of $H_2$ in isobutane, and then being washed with isobutane for another 10 minutes (total washing and regeneration time 2 hours).

After 11 cycles olefin breakthrough was observed. In contrast, when, as described in Example 1, the catalyst was regenerated with isobutane and $H_2$ under comparable conditions, the system did not show a sign of olefin breakthrough even after 40 cycles and could be operated for much longer.

EXAMPLE 2

This example further illustrates the process according to the invention.

The process of Example 1 was repeated, except that this time the catalyst was regenerated every three hours of its operation, at 42% of the active cycle, by being first washed with isobutane for 10 minutes, then regenerated for 340 minutes by being contacted with a solution of 1 mole % of $H_2$ in isobutane, and subsequently washed with isobutane for another 10 minutes (total washing and regeneration time 6 hours). The process conditions during the washing steps and the regeneration step were the same as those prevailing during the reaction step. By operating in this fashion it was possible to achieve a stable process. After 160 hours still no olefin breakthrough had occurred. The average product had substantially the same properties as the product obtained in Example 1. The product obtained after 160 hours was still of good quality.

EXAMPLE 3

This example further illustrates the process according to the invention.

The process of Example 1 was repeated, except that this time the catalyst was regenerated every six hours of its operation, at 85% of the active cycle, by being first washed with isobutane for 10 minutes, then regenerated for 700 minutes by being contacted with a solution of 1 mole % of $H_2$ in isobutane, and subsequently washed with isobutane for another 10 minutes (total washing and regeneration time 12 hours). The process conditions during the washing steps and the regeneration step were the same as those prevailing during the reaction step. By operating in this fashion it proved impossible to achieve a stable process. After 60 hours breakthrough occurred. This experiment indicates that the production time affects the required regeneration time. In all examples the ratio of production time to regeneration time was 1:2. In Examples 1 and 2, carried out with one hour of production and two hours of regeneration and three hours of production and six hours of regeneration, respectively, said ratio made it possible to run a stable process. In the present example, which had six hours of production and 12 hours of regeneration, the production time:regeneration time ratio of 1:2 no longer resulted in a stable process.

By contrast, a stable process was obtained where in the case of six hours of production the production time:regeneration time ratio was raised to 1:3, with the catalyst being regenerated after every six hours of its operation, at 85% of the active cycle, by being first washed with isobutane for 10 minutes, then regenerated for 1060 minutes by being contacted with a solution of 1 mole % of $H_2$ in isobutane, and subsequently washed with isobutane for another 10 minutes (total washing and regeneration time 18 hours).

These examples show that a shorter regeneration time will suffice when the catalyst is regenerated earlier. Accordingly, it is preferred that the catalyst be regenerated as frequently as possible.

EXAMPLE 4

This example illustrates the influence of the presence of a matrix material and the catalyst particle size.

In this experiment, use was made of a microflow reactor, which was filled as follows:

An amount of catalyst corresponding with 5 grams of zeolite calcined at 400° C. was put in a measuring cylinder of 50 ml with an internal diameter of 2.5 cm. Carborundum particles with a particle size of 16 mesh were added to a total volume of 30 ml. The catalyst and the carborundum particles are carefully mixed. A reactor with an internal diameter of 15 mm, equipped with a thermowell with an external diameter of 3mm in the center of the reactor, was filled for the bottom 17 cm with carborundum particles with a diameter of 16 mesh, which were covered with a thin layer of glasswool. Then, the mixture of catalyst and carborundum particles was applied, followed by filling the large spaces in the catalyst bed with fine carborundum (100 mesh) by application of the fine carborundum and tapping against the reactor. The catalyst layer was covered with a thin layer of glasswool, and topped off with 16 mesh carborundum particles. After closing the reactor and purging with nitrogen, the reactor was brought under a $H_2$ flow of 1Nl/min, and heated to 90° C. under atmospheric pressure. The reactor temperature was then raised to 200° C. in about 45 minutes. After 1 hour at 200° C. the temperature was raised to 400° C. at a rate of 2° C./min. After half an hour at 400° C. the reactor temperature was allowed to fall during the night to 90° C., which was the reaction temperature. Then, the pressure was set at 21 bar, and a flow of isobutane, followed by a flow of a mixture of 2% of cis-2-butene in isobutane were started. The catalysts were tested at a temperature of 90° C., a pressure of 21 bar, an olefin weight space velocity of 0.4 h-1, calculated on total zeolite, and a ratio of isobutane to cis-2-butene of 50:1.

The intermittent regeneration was not applied in these microreactor tests, because they are mainly used for fast catalyst screening. Only breakthrough runs were carried out, followed each time by regeneration of the catalyst with gaseous hydrogen at 250° C. and 21 bar. This made it possible to perform successive breakthrough runs with the same catalyst sample.

From comparative runs it has appeared that this test gives results which show the same trends as the results obtained in the cycle reactor used in the other examples.

Five catalysts were tested in this unit, which all contain a USY zeolite loaded with 0.5 wt. % of platinum, and if present, gamma-alumina as the matrix component. The 5 catalysts varied in their matrix content and particle size. The following table gives the tested catalyst compositions, and the test results obtained therewith.

| catalyst parameters | | performance data | | | | | |
|---|---|---|---|---|---|---|---|
| | wt. % $Al_2O_3$ | prt. size (mm) | C5+ yield wt. % | RON | TMP/ DMH | wt. % C9+ | wt. % C8 | wt. % C5–C7 |
| A | 0 | 0.4–0.6 | 226.90 | 90.22 | 2.5 | 13.4 | 56.4 | 30.2 |
| B | 20 | 0.4–0.6 | 223.14 | 90.79 | 2.7 | 17.1 | 55.2 | 27.7 |
| C | 20 | 1.5 | 223.34 | 91.95 | 3.3 | 11.7 | 62.5 | 25.7 |
| D | 35 | 1.5 | 223.49 | 91.81 | 3.3 | 12.4 | 61.3 | 26.3 |
| E | 50 | 1.5 | 223.41 | 91.75 | 3.2 | 12.4 | 61.2 | 26.5 |

From this data it appears that increasing the alumina content of catalyst A from 0 to 20 wt. %, resulting in Catalyst B, results in a RON increase of 0.57 and an increase in TMP/DMH of 0.2, albeit accompanied by a decrease in C5+ yield and C8 selectivity. The addition of a matrix material thus results in a C8-alkylate of better properties.

Increasing the particle size of catalyst B from 0.4–0.6 mm to 1.5 mm extrudates, resulting in catalyst C, results in the same C5+ yield, but an increase in RON of 1.16 and an increase in TMP/DMH ratio of 0.6. The selectivity for C8 increases with as much as 7.3%.

A further increase of the alumina content of the extrudates from 20 wt. % to 35 wt. % (catalyst D) and 50 wt. % (catalyst E), does not influence the performance substantially.

EXAMPLE 5

This example shows the effect of the addition of matrix material and increase in particle size in a process using intermittent catalyst regeneration before deactivation.

This experiment was carried out as described in Example 1. The amount of catalyst was selected such for each experiment that the reactor contained 27 grams of zeolite. In each case, the catalyst was mixed with 60 mesh carborundum particles in a volume ratio of 1:1 on catalyst. In each case, the catalyst was calcined and reduced before use at 400° C.

The cis-2-butene-WHSV was 0.19 $h^{-1}$, calculated on zeolite. The overall rate of flow of liquid in the system was maintained at about 1320 g/h. The molar ratio of isobutane to cis-2-butene was about 250:1. The pressure in the reactor amounted to 21 bar. The reaction temperature was 90° C.

The following catalysts were tested in this system

| | particle size | hydrogenation function | % zeolite | % matrix |
|---|---|---|---|---|
| Catalyst A | 0.4–0.6 mm | 0.5 wt. % Pt | 100% Y-zeolite | — |
| Catalyst C | 1.5 mm | 0.5 wt. % Pt | 80% Y-zeolite | 20% alumina |
| Catalyst D | 1.5 mm | 0.5 wt. % Pt | 65% Y-zeolite | 35% alumina |
| Catalyst F | 3 mm | 0.5 wt. % Pt | 80% Y-zeolite | 20% alumina |

The active cycle of Catalyst A was determined by performing the process under the aforesaid conditions until at least 20% of the butene supplied was found in the product, i.e., at an olefin breakthrough of 20% or higher. Next, interpolation was used to determine the active cycle of the catalyst. Under the conditions stipulated above, the active cycle of Catalyst A turned out to be 7 hours. The active cycles of Catalysts C, D, and F, were determined in the same manner. It appeared that the life cycles of these catalysts are substantially the same as the life cycle of Catalyst A.

After the length of the life cycle had been determined, the catalyst was regenerated with hydrogen at a temperature of 250° C. at a pressure of 21 bar for a period of 1 hour, returning the activity of the catalyst to its original level. The system was then started up again under the same conditions, except that each time after 1 hour of reaction, i.e., at 14% of the active cycle, the catalyst was regenerated by being washed with isobutane for 10 minutes, followed by 100 minutes of regeneration through being contacted with a solution of 1 mole % of $H_2$ in isobutane, and then being washed with isobutane for another 10 minutes (total washing and regeneration time 2 hours). The process conditions during the washing steps and the regeneration step were the same as the process conditions during the reaction step.

The following table gives the properties of the average products obtained during the runs using the various catalysts.

|  | Catalyst A | Catalyst C | Catalyst D | Catalyst F |
|---|---|---|---|---|
| particle diameter | 0.4–0.6 mm | 1.5 mm | 1.5 mm | 3 mm |
| carrier matrix content | 0% | 20% | 35% | 20% |
| Catage | 19.5 | 20.2 | 19.4 | 19.9 |
| C5+ alkylate yield | 227 wt. % | 222 wt. % | 222 wt. % | 222 wt. % |
| RON | 91.9 | 93.9 | 93.8 | 94.1 |
| TMP/DMH | 3.2 | 4.4 | 4.3 | 4.5 |
| wt. % C9+ alkylate | 12 | 8.9 | 11.0 | 7.8 |
| wt. % C8 | 58.2 | 67.5 | 65.4 | 69.0 |
| wt. % C5–C7 | 29.8 | 23.6 | 23.6 | 23.1 |
| Reid vapour pressure | 0.36 bar | 0.30 bar | 0.30 bar | 0.29 bar |
| density | 0.696 g/ml | 0.7006 g/ml | 0.701 g/ml | 0.700 g/ml |

In the table, and in the rest of the specification, the weight percentages of C9+ alkylate, C8, and C5–C7 are calculated on the C5+ alkylate produced. The catage is calculated as a the number of grams of C5+ alkylate produced per gram of zeolite during the run. The values for the Reid vapour pressure and the density are determined from GC-analysis data.

From the above table it can be seen that the use of a matrix-containing catalyst with a particle diameter of 1.5 mm results in a product with a higher RON than a matrix-free catalyst with a particle diameter of 0.4–0.6 mm. Further, the wt. % C9 + alkylate has decreased, which is an indication that the catalyst is more stable. When the particle diameter is further increased to a value of 3 mm, the RON increases even further, while the wt. % C9+alkylate decreases further. When in the 1.5 mm extrudate the matrix content of the carrier is increased from 20 wt. % to 35 wt. %, the quality of the product remains substantially the same.

EXAMPLE 6

This example shows that the stability of the catalyst is improved when the particle size of the catalyst particles increases.

Two catalysts, one with a particle size of 1.5 mm and one with a particle size of 3 mm were tested under the conditions of Example 1. The catalyst with a diameter of 1.5 mm contained 35 wt. % of alumina, while the catalyst with a diameter of 3 mm contained 20 wt. % of alumina. Based on Examples 4 and 5, the presence of additional matrix material to the catalyst particle is not expected to significantly influence the catalytic properties. It is noted that the amount of zeolite in the reactor was the same for both types of catalyst. Therefore, these two experiments are considered comparable.

The following table gives the average product obtained after a certain catage with the respective catalysts. From this table it appears that for the 1.5 mm extrudate the quality of the average product has decreased slightly when the process has been operated for an increasing catage. This is in particular evident from the increase of almost 2 wt. % in the average wt. % of C9+ at a catage of 36.5 as compared to the average weight % of C9+ at a catage of 19.4. In comparison, for the 3 mm extrudate, it appears that the quality of the average product has not decreased when the process has been operated at increasing catage. This is evidenced by the fact that the average wt. % of C9+ at a catage of 34.6 has increased with only 0.1 wt. % as compared to the average weight % of C9+ at a catage of 19.9. It can thus be concluded that the catalyst with a diameter of 3 mm is more stable than the catalyst with a diameter of 1.5 mm.

|  | Catalyst D | Catalyst D | Catalyst F | Catalyst F |
|---|---|---|---|---|
| particle diameter | 1.5 mm | 1.5 mm | 3 mm | 3 mm |
| carrier matrix content | 35% | 35% | 20% | 20% |
| Catage | 19.4 | 36.5 | 19.9 | 34.6 |
| C5+ alkylate yield (wt. %) | 222 | 221 | 222 | 222 |
| RON | 93.8 | 93.7 | 94.1 | 94.1 |
| TMP/DMH | 4.3 | 4.2 | 4.5 | 4.5 |
| wt. % C9+ alkylate | 11.0 | 12.8 | 7.9 | 8.0 |
| wt. % C8 | 65.4 | 64.0 | 69.0 | 69.0 |
| wt. % C5–C7 | 23.6 | 23.2 | 23.1 | 23.0 |
| Reid vapour pressure | 0.30 bar | 0.29 bar | 0.29 bar | 0.29 bar |
| density (g/ml) | 0.701 | 0.702 | 0.700 | 0.700 |

The stability of the catalysts can also be clearly seen from a comparison between FIGS. 1 and 2. FIG. 1 gives for the 1.5 mm extrudate the weight percentage of C9+ formed as function of the run time. FIG. 2 give the same data for the 3 mm extrudate. From these figures it can be seen that the C9+ formation is much more constant for the 3 mm extrudate than for the 1.5 mm extrudate, which indicates an increased stability.

We claim:

1. A process for alkylating hydrocarbons wherein an alkylatable organic compound is reacted with an alkylation agent to form an alkylate in the presence of a catalyst comprising a hydrogenating function and a solid acid constituent, with the catalyst being subjected intermittently to a regeneration step by being contacted with a feed containing a saturated hydrocarbon and hydrogen, said regeneration being carried out at 90% or less of the active cycle of the catalyst, with the active cycle of the catalyst being defined as the time from the start of the feeding of the alkylation agent to the moment when, in comparison with the entrance of the catalyst-containing reactor section, 20% of the alkylation agent leaves the catalyst-containing reactor section without being converted, not counting isomerisation inside the molecule;

wherein said catalyst is regenerated before there is any substantial decrease of activity of said catalyst.

2. The process of claim 1 wherein the alkylatable organic compound is isobutane and the alkylation agent comprises C3–C5 alkenes.

3. The process of claim 2 wherein the alkylation agent is butene or a mixture of butenes.

4. The process of claim 1 wherein the regeneration is carried out at 60% or less of the active cycle of the catalyst.

5. The process of claim 4, wherein the regeneration is carried out at 20% or less of the active cycle of the catalyst.

6. The process of claim 1 wherein the catalyst has a particle size of at least 0.75 mm.

7. The process of claim 6 wherein the catalyst has a particle size of at least 1.5 mm.

8. The process of claim 7 wherein the catalyst has a particle size of at least 2.5 mm.

9. The process of claim 1 wherein the catalyst comprises a hydrogenation function on a carrier comprising 2–98 wt. % of matrix material and the balance solid acid constituent.

10. The process of claim 9 wherein the catalyst carrier comprises 20–80 wt. % of matrix material and the balance solid acid constituent.

11. The process of claim 10, wherein the catalyst carrier comprises 20–50 wt. % of matrix material and the balance solid acid constituent.

12. The process of claim 9 wherein the matrix material comprises alumina.

13. The process of claim 1 wherein the solid acid constituent is a Y-zeolite or zeolite beta.

14. The process of claim 1 wherein the hydrogenation function is a noble metal of Group VIII of the Periodic Table, which is present in an amount of 0.01–2 wt. %, calculated as metal.

15. The process of claim 14 wherein the hydrogenation function is platinum, palladium, or a mixture thereof.

16. The process of claim 1 wherein the saturated hydrocarbon employed in the regeneration is the alkylatable organic compound.

17. The process of claim 16, wherein the regeneration temperature and/or the regeneration pressure do not differ by more than 50% from the reaction temperature, expressed in ° C., and the reaction pressure, respectively.

18. The process of claim 17 wherein the regeneration temperature and/or the regeneration pressure do not differ by more than 20% from the reaction temperature, expressed in ° C., and the reaction pressure, respectively.

19. The process of claim 18, wherein the regeneration is carried out at substantially the same temperature and/or pressure as the reaction.

20. The process of claim 1 wherein the length of the regeneration step is 0.1 to 10 times as long as the length of the reaction step.

21. The process of claim 20 wherein the length of the regeneration step is 0.5–2 times as long as the length of the reaction step.

22. The process of claim 1 wherein the regeneration step is preceded by a washing step with a saturated hydrocarbon essentially in the absence of hydrogen and alkylation agent, is followed by a washing step with a saturated hydrocarbon essentially in the absence of hydrogen and alkylation agent, or both.

23. The process of claim 1 wherein the catalyst is periodically subjected to a high temperature regeneration with hydrogen in the gas phase.

24. The process of claim 23 wherein the catalyst is subjected to a high temperature regeneration with hydrogen in the gas phase after every 50 regenerations with saturated hydrocarbon and hydrogen.

* * * * *